United States Patent
Moon et al.

(10) Patent No.: US 11,091,740 B2
(45) Date of Patent: Aug. 17, 2021

(54) COMPOSITION FOR INDUCING DEDIFFERENTIATION INTO CANCER STEM CELLS COMPRISING RIBOSOME-ACTIVATING INHIBITOR AS ACTIVE INGREDIENT, CANCER ORGANOID CULTURE METHOD AND ANTICANCER DRUG SCREENING PLATFORM BASED THEREON

(71) Applicant: PUSAN NATIONAL UNIVERSITY INDUSTRY-UNIVERSITY COOPERATION FOUNDATION, Busan (KR)

(72) Inventors: Yuseok Moon, Yangsan-si (KR); Seung Joon Lee, Yangsan-si (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 336 days.

(21) Appl. No.: 16/105,978

(22) Filed: Aug. 21, 2018

(65) Prior Publication Data
US 2018/0355323 A1    Dec. 13, 2018

Related U.S. Application Data

(63) Continuation-in-part of application No. PCT/KR2017/002199, filed on Feb. 28, 2017.

(30) Foreign Application Priority Data

Mar. 4, 2016 (KR) .................. 10-2016-0026311

(51) Int. Cl.
*G01N 33/50* (2006.01)
*C12N 5/095* (2010.01)

(52) U.S. Cl.
CPC ....... *C12N 5/0695* (2013.01); *G01N 33/5011* (2013.01); *C12N 2501/11* (2013.01); *C12N 2501/115* (2013.01); *C12N 2501/999* (2013.01); *C12N 2503/02* (2013.01); *C12N 2503/04* (2013.01); *C12N 2506/30* (2013.01); *C12N 2513/00* (2013.01)

(58) Field of Classification Search
CPC .............. C12N 5/0695; C12N 2506/30; C12N 2503/04; C12N 2513/00; C12N 2501/999; G01N 33/5011
See application file for complete search history.

(56) References Cited

U.S. PATENT DOCUMENTS

2014/0308695 A1* 10/2014 Bruce ................ G01N 33/5023
435/26

FOREIGN PATENT DOCUMENTS

KR    10-2015-0054728    5/2015

OTHER PUBLICATIONS

Oh et al (JBC 291:10173-10183, May 2016 (Year: 2016), IDS filed on Aug. 21, 2018.*
Patel et al (Ther. Deliv6:509-520, 2014) (Year: 2014).*
Duan, Xinrui et al., "Discrimination of colon cancer stem cells using noncanonical amino acid", Chemical Communication, 2012, vol. 48, pp. 9035-9037.
Stedman, A. et al., "Ribosome biogenesis dysfunction leads to p53-mediated apoptosis and goblet cell differentiation of mouse intestinal stem/progenitor cells", Cell Death and Differentiation, 2015, vol. 22, pp. 1865-1876.
He, Kaiyu et al., "Targets and Intracellular Signaling Mechanisms for Deoxynivalenol-Induced Ribosomal RNA Cleavage", Toxicological Sciences, 2012, vol. 127, No. 2, pp. 382-390.
Jiang, Xiaojing et al., "Potential Dual Role of Activating Transcription Factor 3 in Colorectal Cancer", Anticancer Rearch, Feb. 2016, vol. 36, pp. 509-516.
Oh, Chang-Kyu et al., "Acquisition of Chemoresistance and Other Malignancyrelated Features of Colorectal Cancer Are Incremented by Ribosome-inactivating Stress", Journal of Biological Chemistry, (Electronic publishing) Mar. 9, 2016, vol. 291, No. 19, pp. 10173-10183.
International Search Report for PCT/KR20171002199 dated Jun. 15, 2017 from Korean Intellectual Property Office.

* cited by examiner

*Primary Examiner* — Lei Yao
(74) *Attorney, Agent, or Firm* — Revolution IP, PLLC

(57) ABSTRACT

A composition for inducing dedifferentiation from cancer cells to cancer stem cells comprising a ribosome-activating inhibitor as an active ingredient, a method of culturing a cancer organoid based thereon and an anticancer drug screening platform, and the increase of colorectal cancer stem cell group induced by the exposure of ribosome-inactivating stress was regulated by the ATF3 gene.

3 Claims, 7 Drawing Sheets

COMPOSITION FOR INDUCING DEDIFFERENTIATION INTO CANCER STEM CELLS COMPRISING RIBOSOME-ACTIVATING INHIBITOR AS ACTIVE INGREDIENT, CANCER ORGANOID CULTURE METHOD AND ANTICANCER DRUG SCREENING PLATFORM BASED THEREON

CROSS REFERENCE TO PRIOR APPLICATION

This application is a Continuation-In-Part Application of International application PCT/KR2017/002199 filed on Feb. 28, 2017, which claims priority to Korean application 10-2016-0026311 filed on Mar. 4, 2016, which is hereby incorporated by reference in its entirety.

BACKGROUND

The present invention relates to a composition for inducing dedifferentiation into cancer stem cells comprising ribosome-activating inhibitor as an active ingredient and a method of inducing dedifferentiation from cancer cells to cancer stem cells using the same. Further, the present invention relates to a cancer organoid culture method and an anticancer drug screening platform based on the composition.

Colorectal cancer (CRC) is one of most commonly diagnosed cancers in the developed countries with high morbidity and mortality rate. This enables late-stage tumors to endow very high metastatic potential to other organs, which is one of the important reasons for early treatment with surgical resection, chemotherapy, and radiotherapy to CRC patients. Although, chemotherapy is the most general and effective strategy of treatment for metastatic colorectal cancer, occasional chemoresistance to anticancer drugs is a serious bottleneck for successful cure.

CRC as an environmental disease is largely influenced by accumulated epithelial stress from diverse environmental causes including ribosome-inactivating stress (RIS). It was postulated that gastrointestinal exposure to RIS may influence malignancy of epithelial tumor cells and their response to anticancer drugs. Meanwhile, the activating transcription factor 3 (ATF3) which is a stress-induced activation factor, is a representative stress-inducing transcription factor which is dependent on the MAPK signal and is increased by ribosome-inactivating stress. In addition, cancer stem cells have been known as a major cause of cancer progression, metastasis, recurrence and resistance to anticancer drugs.

Ribosomal inactivation is known to induce acute and chronic mucosal inflammation and to be a pathogenic factor in human intestinal epithelial inflammatory disease including IBD, however, studies are insufficient on the direct relevance of ATF3 to dedifferentiation into cancer stem cells caused by exposure of ribosome-inactivating stress.

Ten years have passed since the invention of inducible pluripotent stem cell (iPSC) technology and at present, the cell culture market is in a remarkable growth trend. In addition, conventional two-dimensional cell culture and animal test-based anticancer drug screening platforms have been developed in a variety of drug screening platforms close to human physiological activity, due to the inhomogeneity of cancer and the difficulty in simulating in vivo activity of cancer. The representative examples are 3D spheroid culture, organoid culture, lab-on-a-chip and organ-on-a-chip. Considering the development trend of the market environment and related technologies, the productization of cancer stem cell culture media sufficiently guarantee marketability and cancer stem cells induced by ribosome-inactivating stress can be used as a core cell source for various drug screening platforms under development. The cancer stem cell target and tolerance-resistant anticancer drug screening platform established in the present invention has the potential to be used in combination with various drug screening platforms being developed (FIG. 1).

An object of the present invention is to provide a composition for inducing dedifferentiation from cancer cells to cancer stem cells comprising a ribosome-activating inhibitor as an active ingredient and a method of inducing dedifferentiation from cancer cells to cancer stem cells comprising: a step of treating cancer cells with a ribosome-activating inhibitor.

Also, another object of the present invention is to provide a method of forming cancer organoid induced by ribosome-inactivating stress and a method of screening anticancer drug resistance inhibitor using the cancer organoid induced by ribosome-inactivating stress.

SUMMARY OF THE INVENTION

In order to solve the above problems, the present invention provides a composition for inducing dedifferentiation from cancer cells to cancer stem cells comprising a ribosome-activating inhibitor as an active ingredient.

In addition, the present invention provides a method of inducing dedifferentiation from cancer cells to cancer stem cells comprising: a step of treating cancer cells with a ribosome-activating inhibitor.

Also, the present invention provides a method of forming cancer organoid induced by ribosome-inactivating stress comprising: a step of forming spheroids by pretreating cancer cells with a ribosome-activating inhibitor; and a step of forming cancer organoid by culturing formed spheroids.

Further, the present invention provides a method of screening anticancer drug resistance inhibitor comprising: a step of contacting cancer organoid induced by ribosome-inactivating stress formed according to the above method with a test substance; a step of measuring anticancer drug susceptibility to the cancer organoid induced by ribosome-inactivating stress in contact with the test substance; and a step of selecting a test substance having increased anticancer drug susceptibility in the cancer organoid induced by ribosome-inactivating stress by comparing with a control sample.

The present invention relates to a composition for inducing dedifferentiation from cancer cells to cancer stem cells comprising a ribosome-activating inhibitor as an active ingredient, a method of culturing cancer organoid based on the same and a platform for screening anticancer drug and confirmed that increment of colorectal cancer stem cell group induced by ribosome-inactivating stress is regulated by the ATF3 gene. Thus, it is can be applied as a method of predicting the ATF3 transcription factor mediated signaling change induced by ribosome inactivating and the severity of colorectal cancer. It can be used as a platform for screening of anticancer drugs targeting cancer stem cells and drugs of overcoming anticancer drug resistance by easily obtaining cancer stem cell group representing the heterogeneity of cancer by simple chemical exposure, thereby expecting the secure of the potential industrial usefulness. In addition, the present invention relates to a method for constructing cancer organoids from cancer cell lines in unlimited supply economically and easily, and as a standardized drug screening platform, which has high academic and industrial value.

DETAILED DESCRIPTION

Figure 1:
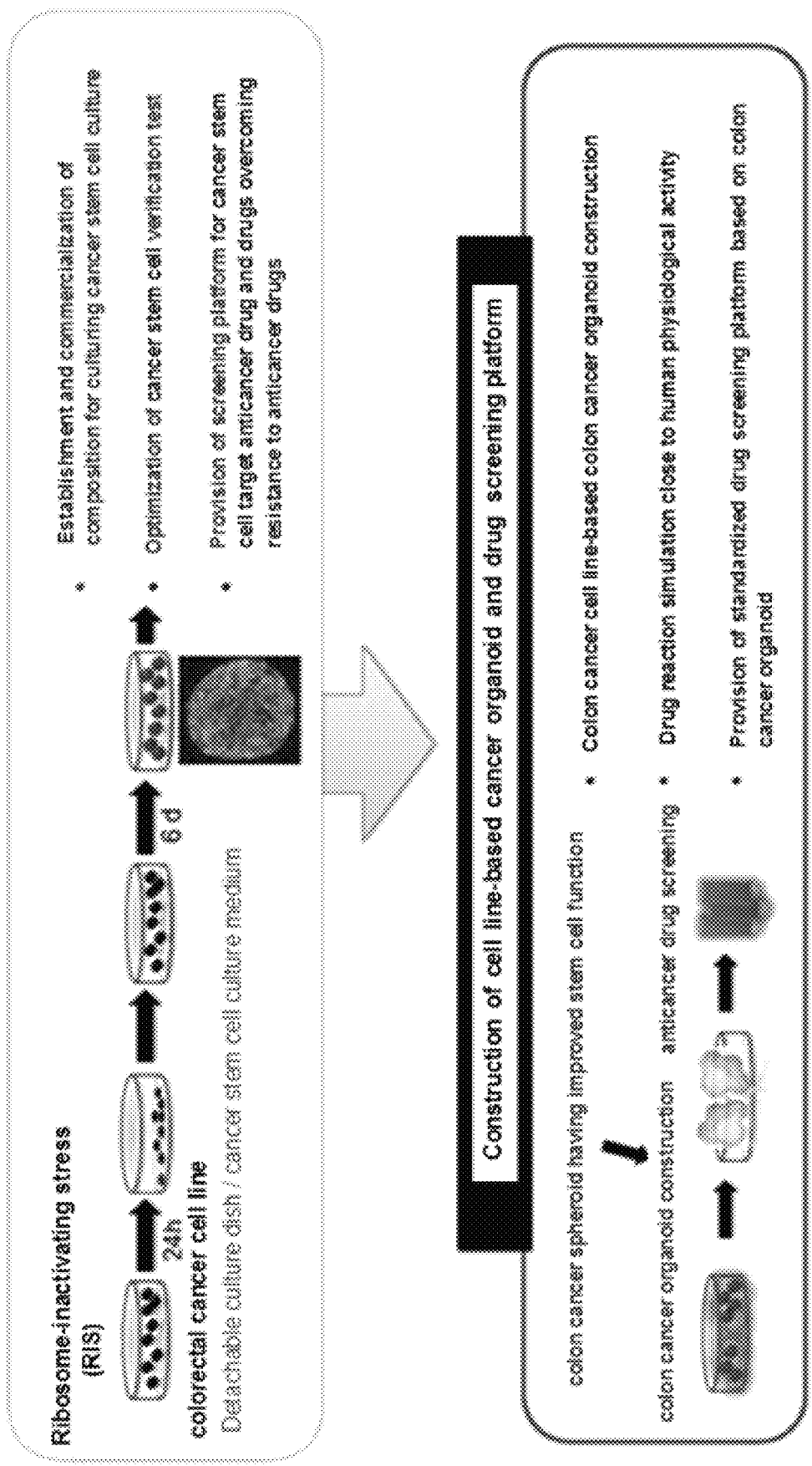
FIG. 1 is a conceptual diagram for development and application of a ribosome-inactivating stress-based colorectal cancer stem cell culture and cancer organoid culture technique.

Thus, the present inventors confirmed that the cancer stem cells exposed to the ribosome-inactivating stress were dedifferentiated and the cancer stem cell group was increased. The inventors developed a method of inducing dedifferentiation to cancer stem cells which is a potential factor of progression, metastasis, recurrence, and resistance to anticancer drug of colorectal cancer by simple chemical exposure using a ribosome-activating inhibitor, and completed the present invention.

Meanwhile, the organoid is a three-dimensional cell aggregate capable of self-renewal and self-organization, and is the most advanced in vitro culture system capable of representing human physiological activity. However, the stem cells (embryonic stem cells, adult stem cells, induced Pluripotent Stem Cells) and cancer tissues (cancer stem cells and circulating tumor cells) which are sources for the organoid cultures have great limit to acquiring maintaining and manipulating. Also, it is costly and time consuming to acquire and maintain it. The cell line can be sub-cultured and supplied indefinitely at a very low maintenance cost, and it is easy to manipulate the gene introduction and deletion, and the conventional 2D cell-based verification technique can be used as it is. When the organoid is constructed from a cell line, it is possible to economically culture the homogenous organoid and to construct an organoid in which a key target gene is deleted, corrected and overexpressed, thereby having very high research value. Thus, the present inventors constructed and developed a standardized drug screening platform because it is possible to reproduce the inherent genetic profile pre-established in the cell line through the cell line-based organoid.

The present invention relates to a method of easily obtaining improved cancer stem cells in terms of purity, yield and survival rate by dedifferentiating epithelial cancer cells exposed to ribosome-inactivating stress, and a proposal for screening platform of drug based on a heterogeneous cancer cell close to human physiological activity. The details are as follows:

Firstly, the present invention establishes a composition for inducing dedifferentiation into cancer stem cells comprising a ribosome-activating inhibitor as an active ingredient, and commercializes optimal environment for culturing the cancer stem cell (culture medium, culture dish, culture additive) and optimizes the validation test method devised for validating the cancer stem cells.

Secondly, this invention can be used as a cancer stem cell-based drug screening platform by simulating a heterogeneous actual cancer cell group comprising a plurality of cancer stem cells. The cancer stem cell-based drug screening platform can be applied as a platform for developing anticancer drug targeting cancer stem cell and anticancer drug overcoming resistance because it targets cancer stem cell which is considered as the main cause of resistance to anticancer drugs, cancer metastasis and recurrence.

Thirdly, the ribosome-inactivating stress in the present invention is non-cancerous, non-genotoxic and reversible, and is a representative stimulus exposed dietary in daily life. Because most of the grains provided to humans and livestock are directly or indirectly exposed to the ribosome-inactivating stresses used in the invention, it is used as a platform for developing medicine for diseases affected greatly by environmental factors such as dietary environment and patterns (gastrointestinal system cancer, various cancers, especially colorectal cancer). This suggests the potential to enter the customized healthcare market.

The present invention provides a composition for inducing dedifferentiation from cancer cells to cancer stem cells comprising a ribosome-activating inhibitor as an active ingredient.

Preferably, the ribosome-activating inhibitor may be anisomycin (ANS, RIS-1) or deoxynivalenol (DON, RIS-2), but is not limited thereto.

Preferably, the dedifferentiation from cancer cells to cancer stem cells may be mediated by activating transcription factor 3 (ATF3), but is not limited thereto.

Preferably, the cancer may be colorectal cancer (CRC), but is not limited thereto.

Also, the present invention provides a method of inducing dedifferentiation from cancer cells to cancer stem cells comprising: a step of treating cancer cells with a ribosome-activating inhibitor.

Preferably, the ribosome-activating inhibitor may be anisomycin (ANS, RIS-1) or deoxynivalenol (DON, RIS-2), but is not limited thereto.

Preferably, the cancer may be colorectal cancer (CRC), but is not limited thereto.

In addition, the present invention provides a method of forming cancer organoid induced by ribosome-inactivating stress comprising: a step of forming spheroids by pretreating cancer cells with a ribosome-activating inhibitor; and a step of forming cancer organoid by culturing formed spheroids.

Preferably, the cancer may be colorectal cancer (CRC), but is not limited thereto Preferably, the ribosome-activating inhibitor may be anisomycin (ANS, RIS-1) or deoxynivalenol (DON, RIS-2), but is not limited thereto.

In the present invention, the term of "organoid" means organ model such as artificial organs manufactured by culturing cells derived from tissues or embryonic stem cells in a 3D form. The organoid has a suffix of "organ" and the meaning of 'similar to organ'. The organoid have a better organized function of cells and cells through the three dimensional culture method and the same shape and function as an organ having functionality. As developing stem cell research and 3D cell culture, the organoid has been attracting attention with optimization studies of growth and differentiation factors that can differentiate into various tissues.

Also, the present invention provides a method of screening anticancer drug resistance inhibitor comprising: a step of contacting cancer organoid induced by ribosome-inactivating stress formed according to the above method with a test substance; a step of measuring anticancer drug susceptibility to the cancer organoid induced by ribosome-inactivating stress in contact with the test substance; and a step of selecting a test substance having increased anticancer drug susceptibility in the cancer organoid induced by ribosome-inactivating stress by comparing with a control sample.

Preferably, the cancer may be colorectal cancer (CRC), but is not limited thereto.

Preferably, the anticancer agent may be fluorouracil (5-FU) or paclitaxel, but is not limited thereto.

The term of "test substance" used in referring to the screening method of the present invention means an unknown candidate substance used in screening to examine whether it affects the expression amount of a gene or affects the expression or activity of a protein. Such samples include, but are not limited to, chemicals, nucleotides, antisense-RNA, siRNA (small interference RNA) and natural extracts.

Hereinafter, the present invention will be described in detail with reference to the following examples. It should be noted, however, that the following examples are illustrative of the present invention and are not intended to limit the scope of the present invention. Embodiments of the present invention are provided to more fully describe the present invention to those skilled in the art.

EXAMPLE 1

Figure 2:
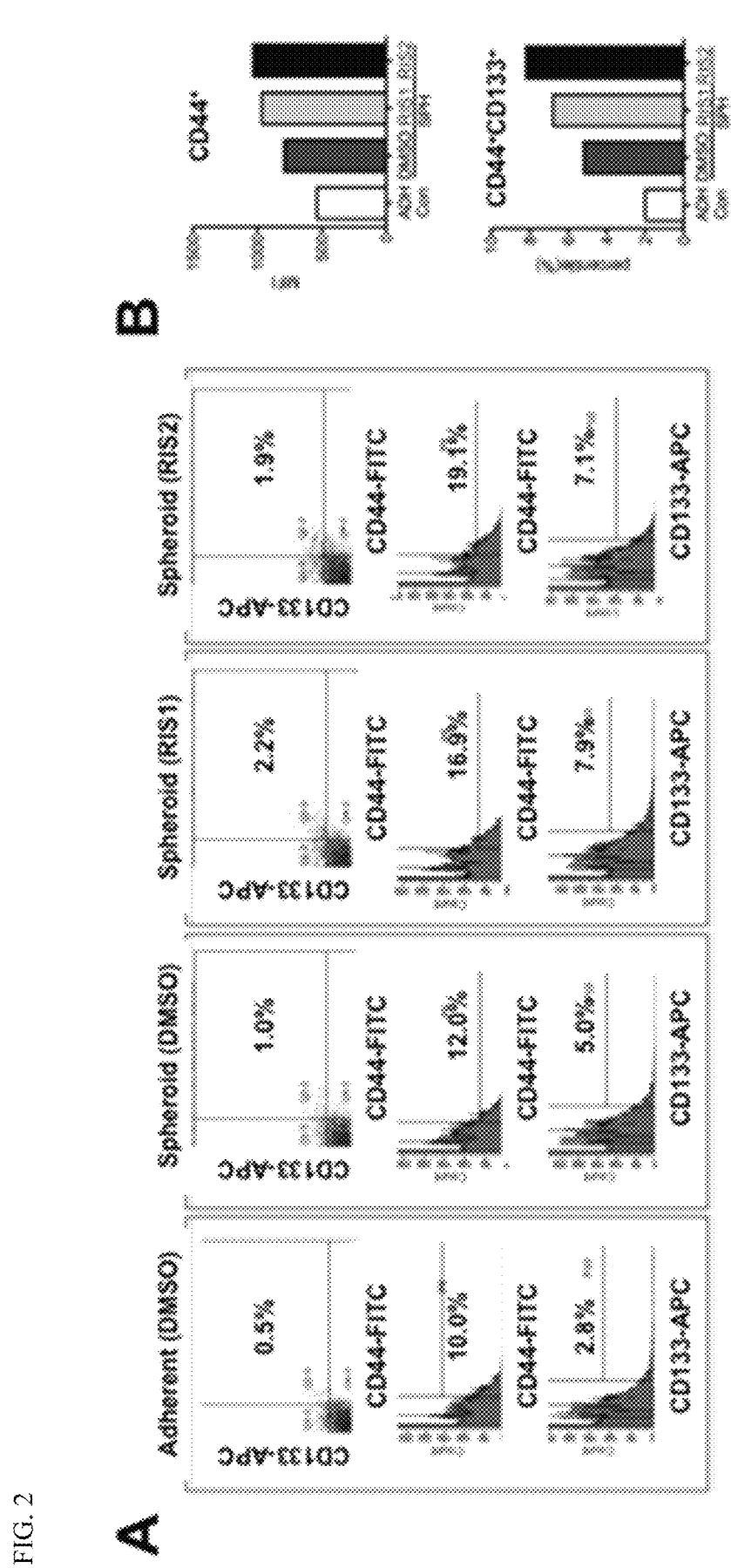
FIG. 2 shows the increment of colorectal cancer stem cell group induced by the ribosome-inactivating stress.

Increase of Stem Cell Group of Colorectal Cancer by Exposure of Ribosome-Inactivating Stress Colon cancer cell lines were purchased from ATCC (Manassas, USA), a cell line distribution company. Cells were maintained with RPMI medium supplemented with 10% (v/v) fetal bovine serum (FBS) and 5% mixed antibiotics (50 units/mL penicillin and 50 mg/mL streptomycin) (welgene, Daegu, South Korea) in a 5% $CO_2$-humidified incubator at 37° C. To combine spheroid culture with ribosome-inactivating stress exposure, colon cancer cell lines were seeded in the ultralow attachment 6-well plate (Costar) and a ribosome-inactivating stress inducer, RIS-1 10 ng/mL or RIS-2 50 ng/mL were pretreated for 6 hours and washed three times with normal RPMI culture medium and cultured in normal RPMI culture medium for 6 days with maintaining the formed spheroid uniformly dispersed (FIG. 2A), Cancer stem cells with high yield and purity were obtained by culturing in DMEM/F12 culture medium (stem cell culture medium) containing B27 (ThermoFisher Scientific), 20 ng/mL EGF (BD), 20 ng/mL bFGF (PEPROTECH, #100-18B), 1% antibiotic to obtain (FIG. 2B). Cancer stem cells heterogeneously present in the formed spheroid cells were identified by CD44 and CD133 antibodies, markers for colorectal cancer stem cell. First, the cultured spheroid cells were dissociated into single cells by trypsinization, washed with phosphate buffer solution, incubated with FITC-conjugated CD44 (BD pharmingen) and APC-conjugated CD133 (MACS, Miltenyi Biotec) antibodies for 15 min, and then the expression of CD44 and CD133 positive cells was analyzed by flow cytometry (Becton Dickinson FACS Canto Il BD Bioscience, San Jose, Calif., USA). When colorectal cancer spheroid cells were exposed to the ribosome inactivating stress, CD44 and CD33 positive cells representing cancer stem cell group were significantly increased comparing with a control (FIGS. 2A and 2B). As shown in FIG. 2B, the basic composition ratio of cancer stem cells was increased together with improving to optimum medium of the cancer stem and when the cancer cells were exposed to the ribosome-inactivating stress, the cancer cells were dedifferentiated to further increasing the proportion of these cells. It suggests that chemical exposure of the ribosome-activating inhibitor can dedifferentiate cancer cells to cancer stem cells.

EXAMPLE 2

Figure 3:
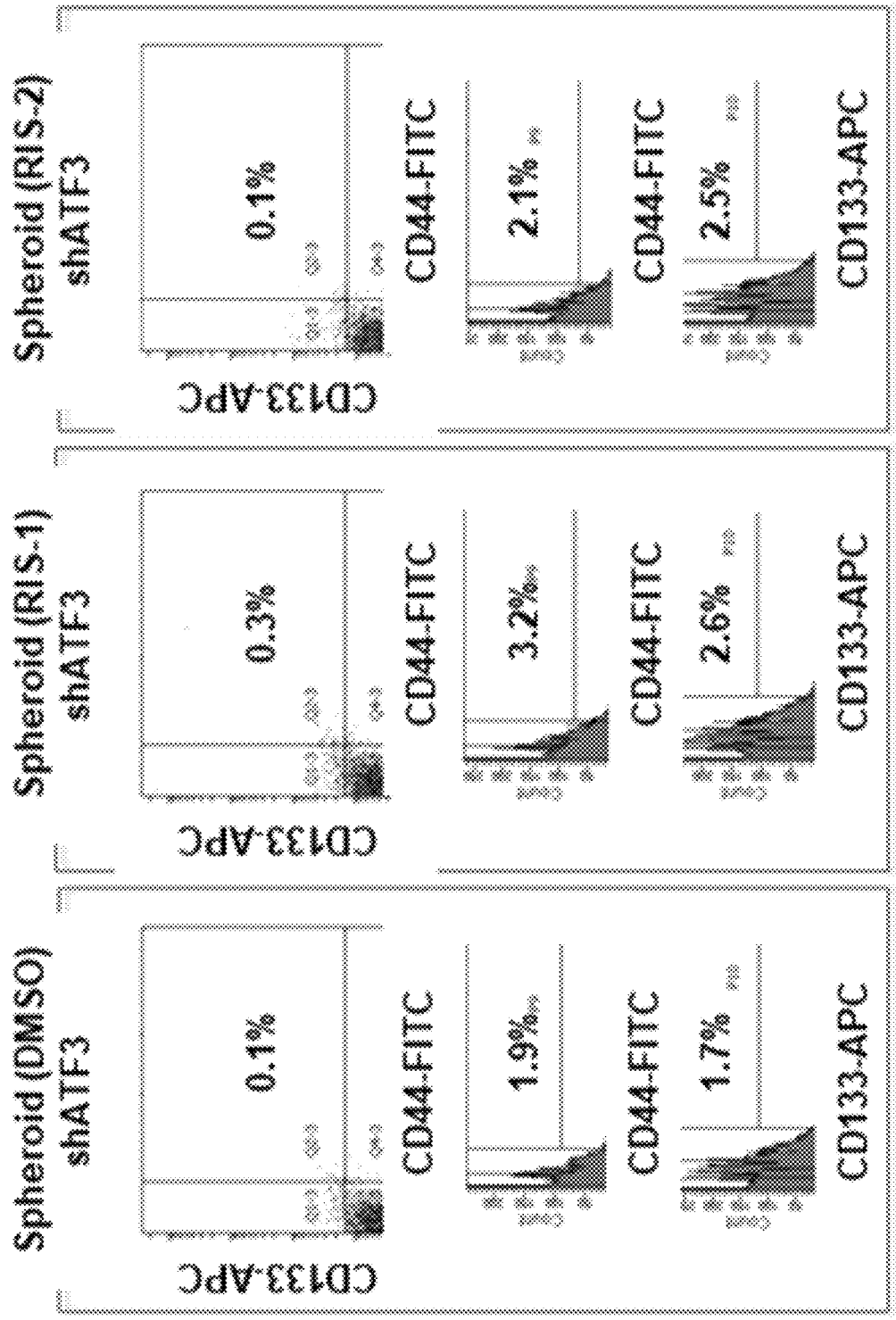
FIG. 3 shows the inactivation of the cancer stem cell group induced by the ribosome-inactivating stress in ATF3-inhibited cancer cells.

ATF3 Gene Regulating Dedifferentiation to Colorectal Cancer Stem Cells by Exposure to Ribosome-Inactivating Stress ATF3 transcription factor is a representative stress-induced factor that is dependent on the MAPK signal and is increased by ribosome-inactivating stress. The ATF3-deficient colorectal cancer cell lines were exposed to ribosome-inactivating stress while spheroid-culturing, in order to confirm the direct relationship between ATF3 and the dedifferentiation to cancer stem cells by exposing to ribosome-inactivating stress. Colorectal cancer stem cells detected by CD44 and CD133-specific antibodies were analyzed and quantified by flow cytometry. ATF3-deficient cells did not significantly increase the number of cell group dedifferentiated to cancer stem cells despite exposure to ribosome-inactivating stress (FIG. 3). This suggests that ATF3 transcription factor plays an important role in regulating the process of dedifferentiation to cancer stem cells by ribosome-inactivating stress.

EXAMPLE 3

Figure 4:
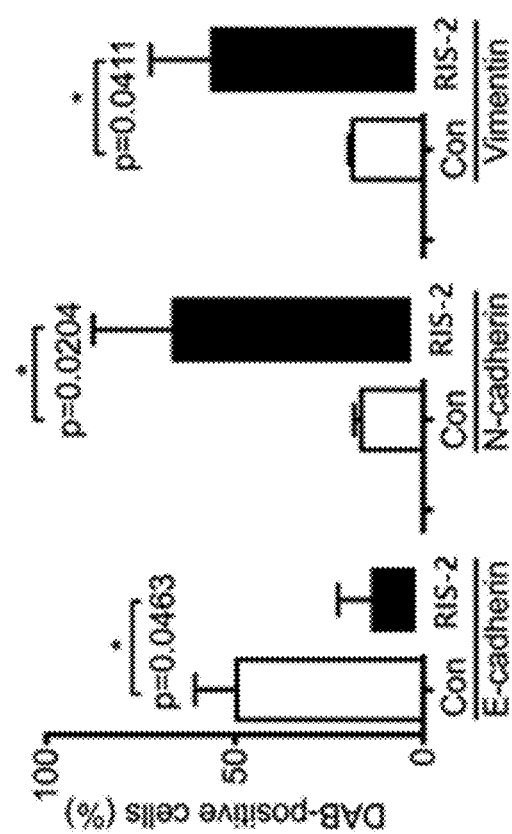
FIG. 4 shows in vivo activity of the cancer stem cell induced by the ribosome-inactivating, i.e. the increment of the Epithelial to Mesenchymal Transition inducing cancer worsening, metastasis and recurrence.
Figure 4:
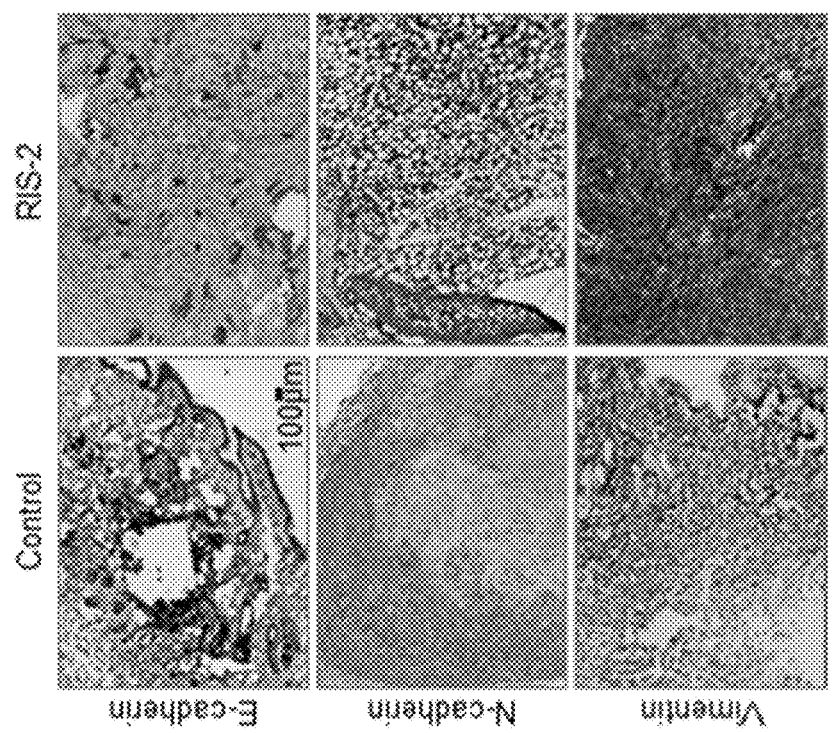

Identification of Bioactivity of Dedifferentiation Process of Colorectal Cancer Stem Cells by Exposure to Ribosome-Inactivating Stress Cancer stem cells have been identified as a major cause of cancer progression, metastasis, recurrence, and resistance to anticancer drugs. In order to investigate the in vivo activity of cancer stem cells produced by the exposure to ribosome-inactivating stress, epithelial mesenchyme transition (EMT) phenomenon, which is an in vivo phenotype representing the characteristics of cancer stem cells was examined. The in vivo activity of cancer stem cells was determined by the degree of epithelial mesenchyme transition, which is verified by the decrease of E-cadherin, an epithelial cell marker and the increase of the protein expression of N-cadherin and vimentin, mesenchymal marker. For this purpose, in vivo experiment using allografts of cancer cells was performed. The CMT-93 mouse colorectal cancer cell line was cultured in DMEM (Welgene, Daegu, South Korea) supplemented with 10% (v/v) fetal bovine serum (FBS) and 5% mixed antibiotics (50 units/mL penicillin, 50 mg/mL streptomycin) in a 5% $CO_2$, 37 humidified incubator at 37° C. CMT-93 cells ($5\times10^6$) pretreated with RIS-2 (50 ng/mL) for 6 hours were resuspended with 200 μL of PBS and injected subcutaneously into a 14-week-old male C57BL/6 mice. Seven days later, 100 mg/mL anticancer drug 5-FU was intraperitoneally injected and tumors were excised surgically 24 h later. Solid tumors were obtained by immunohistochemistry using E-cadherin (1:200, BD Science), N-cadherin (1:200, BD Science), vimentin (1:200, Cell signaling) specific antibodies. The excised solid tumors were fixed in 4% paraformaldehyde, embedded in paraffin, and sectioned to prepare slice slide specimens. After dehydration and antibody binding, spatial expression of protein expression in tissues was investigated by 3,3-diaminobenzidine (DAB) substrate reaction and relative expression of DAB versus hematoxylin-positive cells was quantified by a tissue analysis software (Histo Quest, TissueGnotics). As shown in FIG. 4, in the case of solid tumors from cells exposed to RIS-2, the epithelial cell marker E-cadherin decreased, and the mesenchymal cell marker N-cadherin and vimentin protein were significantly increased. This result shows that the dedifferentiation of cancer cells into cancer stem cells caused by the exposure of ribosome-inactivating stress has in vivo activity.

EXAMPLE 4

Figure 5:
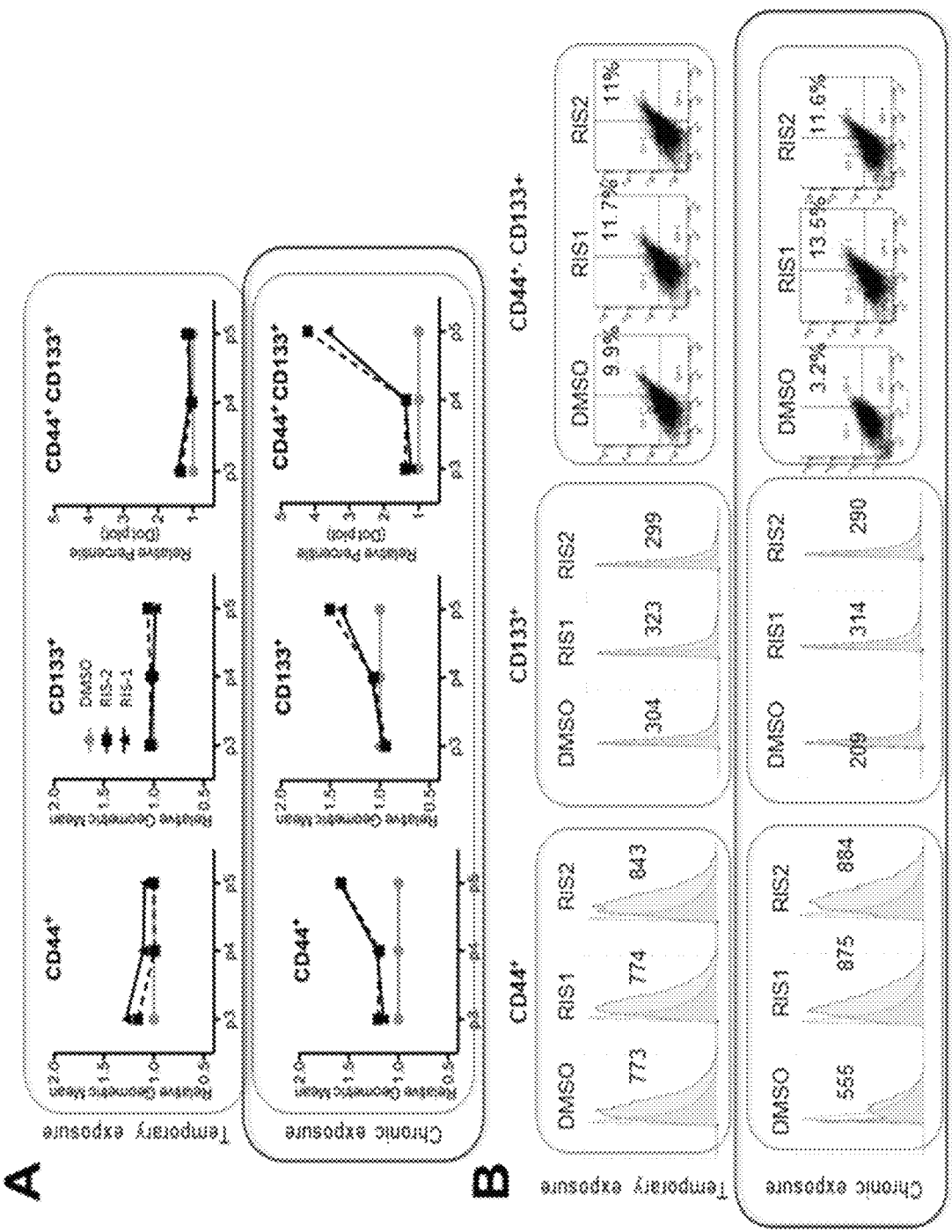
FIG. 5 shows the results of the revalidation and verification of optimization of the colorectal cancer stem cell group induced by ribosome-inactivating stress.

Establishment of a Test Method for Increasing Colorectal Cancer Stem Cell Group by Repetitive Exposure to Ribosome-Inactivating Stress To reconfirm that ribosome-inactivating stress (RIS1, RIS2) is a key factor for inducing the dedifferentiation of epithelial cancer cells, the cells were exposed to ribosome-inactivating stress once for 24 hours, spheroid cultured in a stein cell culture medium for 6 days. In the experimental groups which sub-cultured in three times; and sub-cultured while exposing to the ribosome-inactivating stress on the optimum medium for cancer stem cell in each subculture (total of 3 exposures), cancer stem cells were compared quantitatively by flow cytometry with CD44 and CD133 as the marker thereof. As shown in FIG. 5, it was confirmed that the cancer stem cells were maintained continuously since a first temporary exposure to the ribosome-inactivating stress, and the CD44 and CD133 positive stem cell groups was increased significantly in chronic exposure by repeated exposure.

EXAMPLE 5

Figure 6:
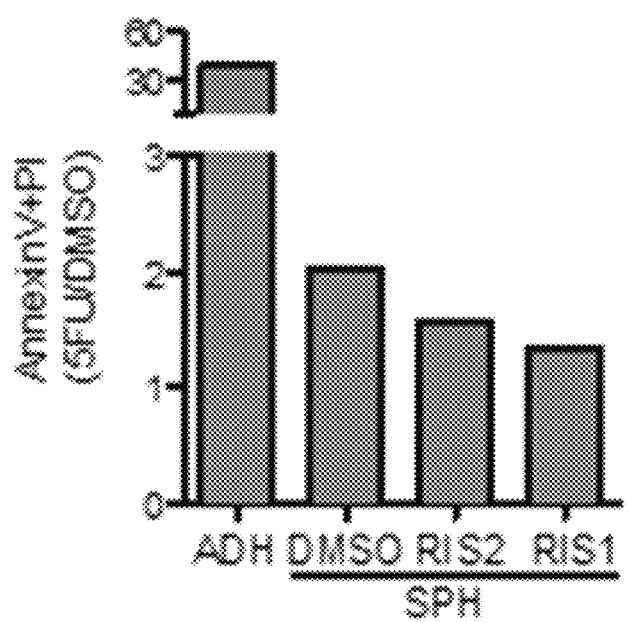
FIG. 6 shows a verification test method of drug response based on ribosome-inactivating stress-induced cancer stem cell and screening of drugs for overcoming resistance to anticancer drug.

Drug Response Based Cancer Stem Cell Induced by Ribosome-Inactivating Stress and Screening Test for Drugs Overcoming Resistance to Anticancer Drugs The drug effect close to human physiological activity can be confirmed by monitoring the anticancer drug response of heterogeneous cancer cells containing a plurality of cancer stem cells induced by the exposure of ribosome-inactivating stress. By verifying this, it is suggested that the present invention can be used as a platform for screening cancer stem cell targets and drugs overcoming resistance to anticancer drugs. Cancer stem cell cultured spheroid were treated with 5-FU (375 μM) for 48 hours and apoptotic cells were quantified by flow cytometry using propidium iodide (PI) and AnnexinV-FITC (1:200) as markers. The number of apoptotic cells positive for both PI and AnnexinV for 5-FU was higher in the control (−) group, but the drug reactivity was better, but those in the general spheroid culture (DMSO) were decreased. In the case of spheroid containing cancer stem cell group induced by ribosome-inactivating stress, the drug reactivity was further reduced. This suggests that drug reactivity was lowered by cancer stem cells induced by ribosome-inactivating stress (FIG. 6). By using this method, it is possible to screen for a drugs which do not respond to the inhibitory effect of the apoptosis. This suggests that it could be used as a screening platform for drug candidates having potential as anticancer drugs to overcome resistance and cancer stem cell target anticancer drugs.

EXAMPLE 6

Cell Line-Based Cancer Organoid Construction

Figure 7:
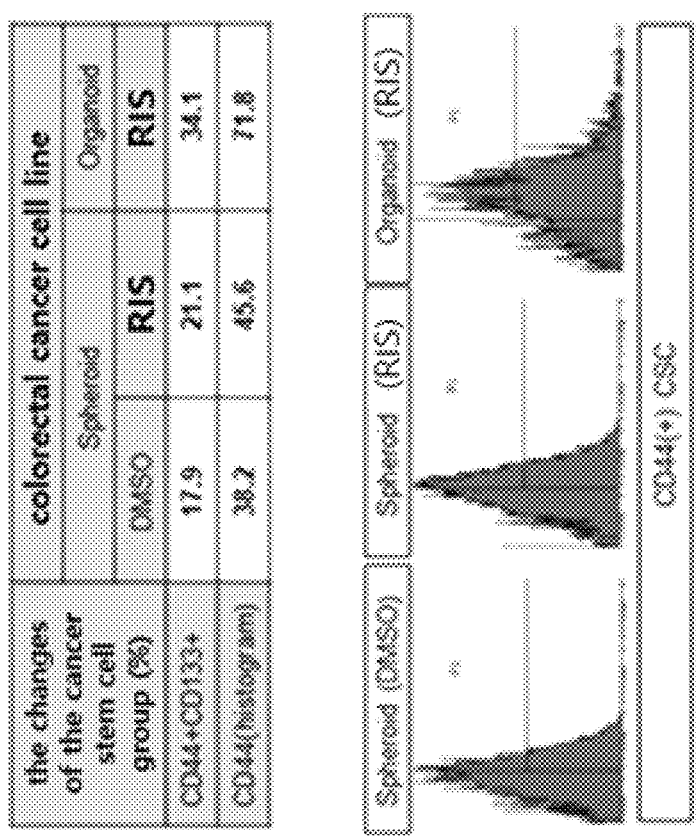
FIG. 7 shows a construction of cancer cell line-based cancer organoid and verification results of cancer stem cells.
Figure 7:
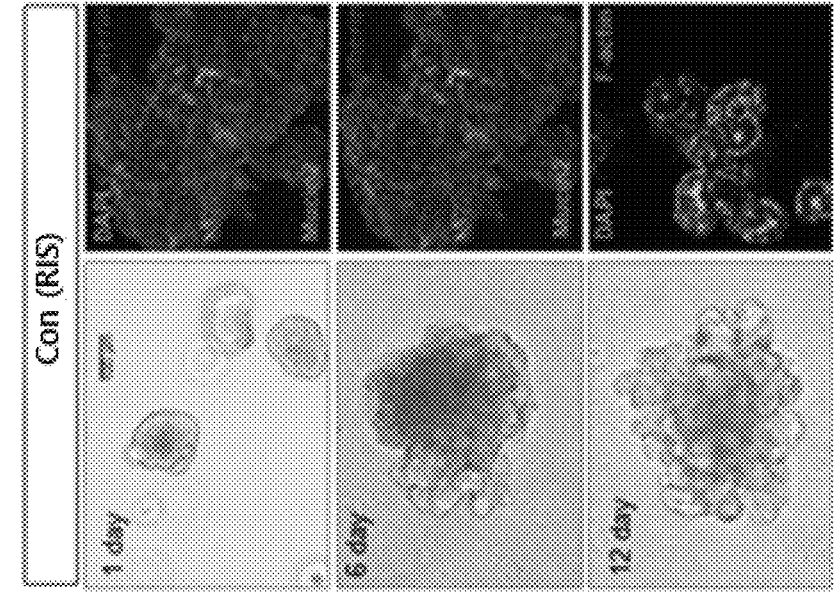

Colorectal cancer cell lines were pretreated with ribosome-inactivating stress, RIS-1 of 10 ng/mL or RIS-2 of 50 ng/mL for 6 hours to form spheroid. Cancer organoid is formed by using spheroid induced from cancer stem cells increased by the ribosome-inactivating stress. A cancer organoid culture technique was developed from cancer stem cells increased by ribosome-inactivating stress. 100 μl of a culture medium containing 200-400 spheroid cells of about 100 μm in size among the cultured spheroids was mixed with an equal amount of a ice-cold matrigel (BD #35424, USA) and divided as a dome in a 24-well culture dish preheated in the cell incubator. Organoid formation (changes in crypt-villus domain production, morphology and size changes, etc.) is monitored by filling the organoid culture medium (STEMCELLS) so as not to reach the cell-matrigel dome and incubating for 12 days (FIG. 7A). The final cultured organoid is tested by immunohistochemistry and flow cytometry. After washing with ice-cold PBS, the organoid was separated from the matrigel and fixed with 0.1% tritonX-100, 4% PFA and immunostained. E-cadherin, an epithelial cell factor, mucin-2, a goblet cell marker for differentiated intestinal cells and F-actin for confirming cell structure formation are examined to confirm the formation of an intestinal organoid (FIG. 7A). To verify the changes of the cancer stem cell group, cultured cancer organoid was separated into single cells, and the change of CD44 (+) cells was examined by flow cytometry (FIG. 7B). As shown in FIG. 7, the cultured organoid showed a typical morphological change of the intestinal organoid, and confirmed the expression of the structured forms of E-cadherin, Mucin-2 and F-actin. CD44 (+) cancer stem cell group was also significantly increased.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of screening anticancer drug resistance inhibitor comprising:
    a step of forming spheroids by pretreating cancer cells with ribosome-inactivating agent anisomycin (ANS, RIS-1) or deoxynivalenol (DON, RIS-2);
    a step of forming cancer organoid induced by ribosome-inactivating stress by culturing the formed spheroids;
    a step of contacting the formed cancer organoid induced by ribosome-inactivating stress with a test substance;
    a step of measuring anticancer drug susceptibility to the cancer organoid induced by ribosome-inactivating stress in contact with the test substance; and
    a step of selecting a test substance having increased anticancer drug susceptibility in the cancer organoid induced by ribosome-inactivating stress by comparing with a control sample.

2. The method of screening anticancer drug resistance inhibitor of claim 1, wherein the cancer is colorectal cancer (CRC).

3. The method of screening anticancer drug resistance inhibitor of claim 1, wherein the anticancer drug is fluorouracil (5-FU) or paclitaxel.

\* \* \* \* \*